(12) United States Patent
Mihali et al.

(10) Patent No.: US 10,426,672 B2
(45) Date of Patent: Oct. 1, 2019

(54) MOISTURE DETECTION AND NOTIFICATION SYSTEM

(71) Applicant: Vener8 Technologies, Southport, CT (US)

(72) Inventors: Raul C. Mihali, Westport, CT (US); Dorin E. Calbaza, Cohoes, NY (US); Jonathan A. Glass, Riverside, CT (US); Anton R. Simunovic, Westport, CT (US)

(*) Notice: Subject to any disclaimer, the term of this patent is extended or adjusted under 35 U.S.C. 154(b) by 0 days.

(21) Appl. No.: 15/677,660

(22) Filed: Aug. 15, 2017

(65) Prior Publication Data

US 2018/0055697 A1    Mar. 1, 2018

Related U.S. Application Data

(60) Provisional application No. 62/380,085, filed on Aug. 26, 2016.

(51) Int. Cl.
| | |
|---|---|
| *A61F 13/42* | (2006.01) |
| *G08B 21/20* | (2006.01) |
| *G08B 21/22* | (2006.01) |
| *G01N 27/22* | (2006.01) |

(52) U.S. Cl.
CPC .......... *A61F 13/42* (2013.01); *G08B 21/20* (2013.01); *G08B 21/22* (2013.01); *A61F 2013/424* (2013.01); *G01N 27/223* (2013.01)

(58) Field of Classification Search
CPC . A61F 13/42; A61F 2013/424; G01N 27/223; G08B 21/20; G08B 21/22
See application file for complete search history.

(56) References Cited

U.S. PATENT DOCUMENTS

| | | | |
|---|---|---|---|
| 4,347,503 A | 8/1982 | Uyehara | |
| 4,646,066 A | 2/1987 | Baughman et al. | |
| 5,266,928 A | 11/1993 | Johnson | |
| 5,469,145 A | 11/1995 | Johnson | |
| 6,373,263 B1 | 4/2002 | Netzer | |
| 6,916,968 B2 | 7/2005 | Shapira | |
| 7,492,270 B2 | 2/2009 | Veerasamy | |
| 8,826,473 B2 | 9/2014 | Flanagan et al. | |
| 9,314,381 B2 | 4/2016 | Curran et al. | |
| 2013/0041334 A1* | 2/2013 | Prioleau | A61F 13/42 604/361 |
| 2013/0194071 A1* | 8/2013 | Slogedal | G06K 9/0002 340/5.82 |
| 2014/0296808 A1* | 10/2014 | Curran | A61F 13/42 604/361 |

FOREIGN PATENT DOCUMENTS

| | | |
|---|---|---|
| CA | 2969780 A1 | 6/2016 |
| WO | WO/2010/123425 A1 | 10/2010 |
| WO | WO/2013/091728 A1 | 6/2013 |

* cited by examiner

*Primary Examiner* — Mohamed Barakat
(74) *Attorney, Agent, or Firm* — Meagher Emanuel Laks Goldberg & Liao, LLP

(57) ABSTRACT

The present invention is directed to a system and apparatus for detecting moisture or fluid using a processing unit and a sensor pad comprising interdigitated conductive leads connected to a coupling unit. The processing unit and coupling unit may be connected wirelessly or via wires. The presence of moisture or fluid may be determined as a function of at least one aspect of the complex impedance as determined by a signal analysis unit.

19 Claims, 16 Drawing Sheets

MOISTURE DETECTION AND NOTIFICATION SYSTEM

CROSS-REFERENCE TO RELATED APPLICATIONS

This application claims benefit of U.S. Provisional Application No. 62/380,085, filed Aug. 26, 2016, and is hereby incorporated in its entirety by reference.

TECHNICAL FIELD

This invention relates to a system and method for detecting and signaling the presence of moisture, such as biofluids, especially in hospitals, long-term care facilities, post-acute care facilities, or home healthcare settings.

BACKGROUND ART

Pressure ulcers, also known as pressure sores, decubitus ulcers, pressure injuries and bedsores, are a significant patient care issue in acute and post-acute care settings. Pressure ulcers are injuries to the skin and surrounding tissues resulting from prolonged pressure in one area of the skin and typically result from a patient sitting or lying in one position for too long while bedridden or wheel chair confined. In the U.S. alone, these injuries affect 2.5 to 3 million adults and result in approximately 60,000 deaths annually from related complications and infections. Accordingly, pressure ulcers place a significant financial burden on U.S. healthcare resources. In the U.S., the Centers for Medicare & Medicaid Services has estimated that each pressure ulcer case adds $43,180 in hospital costs and that pressure ulcers overall add up to $11 billion in annual costs to the U.S. healthcare system. Moreover, pressure ulcers are the second most common claim after wrongful death against U.S. healthcare providers and account for 17,000 lawsuits annually.

Prolonged patient exposure to moisture—such as moisture from urinary or diarrheal incontinence—can accelerate the development of a pressure ulcer or exacerbate an existing injury. Thus, real-time detection of a moisture event and notification to nursing personnel may have a significant positive impact in reducing pressure ulcer incurrence and/or severity and lead to improved quality of care and reduced financial and legal burdens for acute, post-acute and long-term care providers.

However, no commercially-available clinical moisture detection and notification system exists that is (i) easy to use, and performance- and cost-effective for the care provider, and (ii) comfortable and unobtrusive for the patient. Further, commercially-available solutions typically require contact with the patient, indenting the skin or causing irritation, or require contact with the moisture itself. When contacting the moisture itself, a portion of the system must be cleaned, sterilized or discarded after each moisture event, thus increasing costs and requiring additional time from the care provider staff to replace the cleaned, sterilized or discarded portion and ensure the system is functioning properly. In addition, commercially-available solutions that are designed as moisture sensing bed pads cannot be used with a disposable incontinence pad (also know as a dry pad or medical chuck), which is often the standard of care for incontinent patients to protect against skin injury—the sensing pad will not work if placed underneath the incontinence pad as moisture will never reach it (all the moisture is absorbed and retained by the incontinence pad). Finally, current moisture detection systems typically do not gather additional data on patient movement and respiratory rates and thus do not meet healthcare providers' needs for the integrated tracking and reporting of data relating to patient incontinence, movement, and respiration.

Thus, there remains a considerable need for devices and methods that can provide an easy to use, cost-effective solution for detecting a patient moisture event without contacting either the patient or the moisture itself and for notifying the appropriate individuals that a moisture event has occurred.

SUMMARY OF INVENTION

The present invention is directed to methods and apparatus for detecting moisture using a processing unit and a sensor pad comprising interdigitated conductive leads connected to a coupling unit.

Among the many different possibilities contemplated, the coupling unit and the processing unit may communicate in a wired or wireless fashion. It is also contemplated that the coupling unit could contain one or more sensors, which include but are not limited to accelerometers, temperature sensors, and humidity sensors.

Although not required, it is contemplated that the processing unit could be configured to communicate with a server, database, or other device, either directly or indirectly through a network. In some embodiments, the processing unit comprises a signal analysis unit.

The conductive leads may or may not be formed into a single layer. It is further contemplated that the interdigitated conductive leads may form multiple zones where different combinative pairs of conductive leads are interdigitated, including but not limited to configurations where the number of zones is less than or equal to $n(n-1)/2$ (n is the number of conductive leads), or where the number of zones is equal to or greater than the number of conductive leads. It is further contemplated that the zones can be varying sizes, although a preferred embodiment utilizes zones having substantially similar areas. It is further contemplated that the fingers of the interdigitated portions of the conductive leads can also be of varying sizes, although a preferred embodiment utilizes fingers wherein the fingers within each zone are all of substantially similar size. It is further contemplated that the sensor pad can be separated from a source of moisture by at least one substrate. In one preferred embodiment, the conductive leads are separated from the source of moisture by a bedsheet, incontinence pad, diaper, an article of clothing, or other layer capable of preventing or delaying the moisture from contacting the sensor pad. It is also contemplated that the sensor pad could be configured to substantially maintain the spacing between each pair of conductive leads when the sensor pad is deformed, or configured such that the coupling unit is attachable to a patient support structure at or substantially at an edge of the patient support structure.

It is further contemplated that the moisture detection system can be configured to determine, estimate, or categorize several data points, including but not limited to (1) the presence or position of a person based on at least one measured impedance, (2) a state of each zone based on the impedances where the states may include but are not limited to the presence/non-presence of a person and/or the presence/non-presence of moisture, (3) at least one of an individual's respiratory rate, body position, or sleeping pattern based on data from the accelerometer, or (4) the volume of a moisture event.

It is also contemplated that the conductive leads can be disposed on a wide range of substrates, from a polymer film to an interior or exterior surface of a mattress, cushion, other patient or individual support surfaces, or an article of clothing.

It is contemplated that these sensor pads can function by measuring at least a first impedance value via the sensor pad, receiving a signal representative of the first impedance value at the processing unit, determining at least one aspect of a first real and imaginary impedance, sending a signal representative of the at least one aspect of the first real and imaginary impedance to a server, database, or other device, receiving the signal representative of the at least one aspect of the first real and imaginary impedance from the processing unit, and determining the presence of moisture based on a function of at least one of a threshold and the at least one aspect of the first real and imaginary impedance. In these embodiments, while many communication approaches are envisioned, one preferred method further allows that the processing unit could also send a unique identification of the processing unit to the server, database, or other device, and wherein the server, database, or other device determines the appropriate individual or individuals for receiving notification of the event based in part on the unique identification of the processing unit. In other embodiments, the processing unit makes the determination of who the appropriate individual(s) are and sends the notification.

In practice, it is contemplated that a person could place the sensor pad in a position where it could detect a moisture event, typically by covering a location where a biofluid could be discharged by an individual. The sensor pad would then be connected to the processing unit physically or electronically, and an absorbent article would be placed between the source of moisture and the sensor pad, such absorbent article including but not limited to a bed sheet, diaper, incontinence pad, or article of clothing. The appropriate individual(s) would receive a notification when a moisture event had occurred.

DESCRIPTION OF EMBODIMENTS

Figure 1:
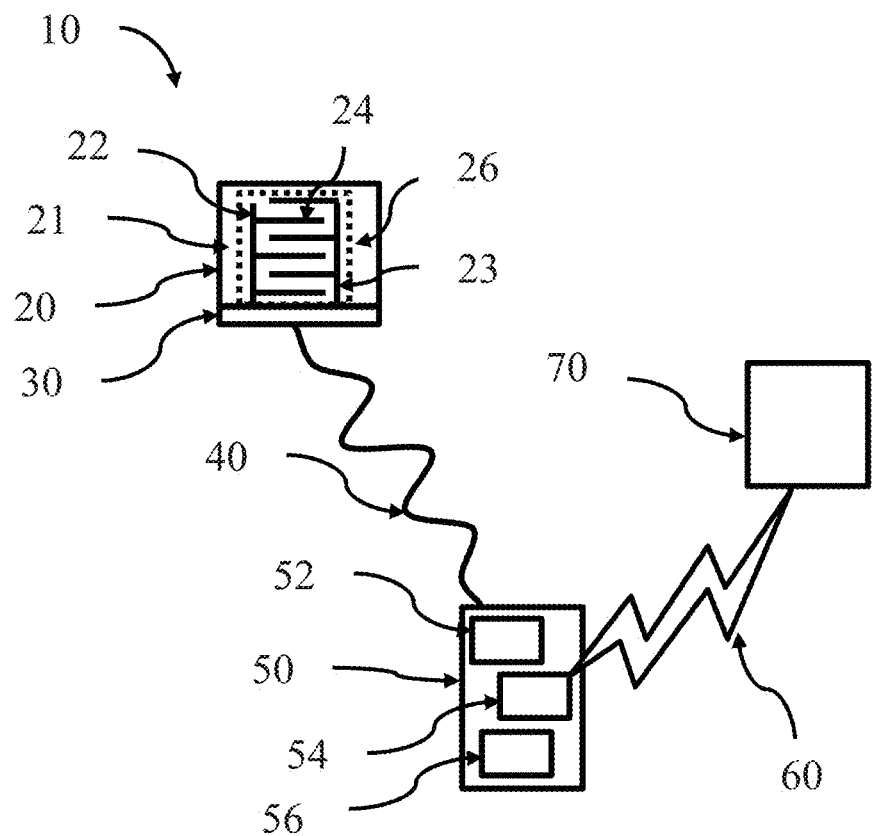
FIG. 1 is an illustration of an embodiment of a moisture detection system.

FIG. 1 generally depicts one embodiment of a moisture detection system (10). The system comprises a sensor pad (20), which itself comprises a first substrate (21) and a plurality of conductive leads (22, 23) disposed on the first substrate and defining at least one zone (26), each zone defined by an area in which fingers (24) of one conductive lead (22) are interdigitated with fingers of another conductive lead (23), and a coupling unit (30) coupled to at least two conductive leads.

In preferred embodiments, the conductive leads are formed in a single layer, via known fabrication techniques. However, other embodiments that utilize multiple deposition layers are also envisioned.

This embodiment depicts a single zone having a very simple pattern of conductive leads. When designing these types of systems, the first consideration is what coverage area is required. For example, a wheelchair seat or chair seat might only require a 20 inch×15 inch coverage while a bed might require a 40 inch×70 inch coverage. While the typical solution to this is to have multiple sensors, this adds significant complexity to the system. A single sensor, such as a single sensor pad, is a simpler and more cost-effective approach. However, with a single sensor, there is a tradeoff between sensitivity and coverage—to get more coverage, you need a bigger sensor, but a bigger sensor is less sensitive. There might be situations in which a single sensor with a single zone is simply not sensitive enough. For example, a 20 inch×30 inch single-zone sensor pad (600 square inches) might show mean impedance values of 80 ohms and 50 ohms for dry and wet states, respectively, a 37.5% difference. When that same size pad is configured to have (as an example) 5 zones of 120 square inches each, the mean impedance values might be 60 ohms and 20 ohms for dry and wet states, respectively, a 67% difference. Because there is variation around the mean, that greater relative difference for the smaller zones of a multi-zone pad makes the wet and dry states more distinct and increases accuracy. In addition, the power required to send a sufficient current through the conductive leads to generate a measurable radio frequency field increases as the size of the sensing zone increases. Thus, if a single large zone is instead sub-divided into smaller zones which is then sampled sequentially, lower power can be used to sample each zone. This is important as many health care regulatory agencies, such as the FDA, and product safety certification bodies, such as UL, have strict medical device power-use requirements to minimize potential interference with other devices or potential electrical shock to the patient.

Having multiple zones can create other issues, as typically each zone would require two additional conductive leads. In some embodiments, that may not be of concern. However, in other embodiments, the pattern of conductive leads is configured to allow more zones with the same number of leads. In some embodiments, the number of zones is less than or equal to $n(n-1)/2$, where n is the number of conductive leads.

Figure 2:
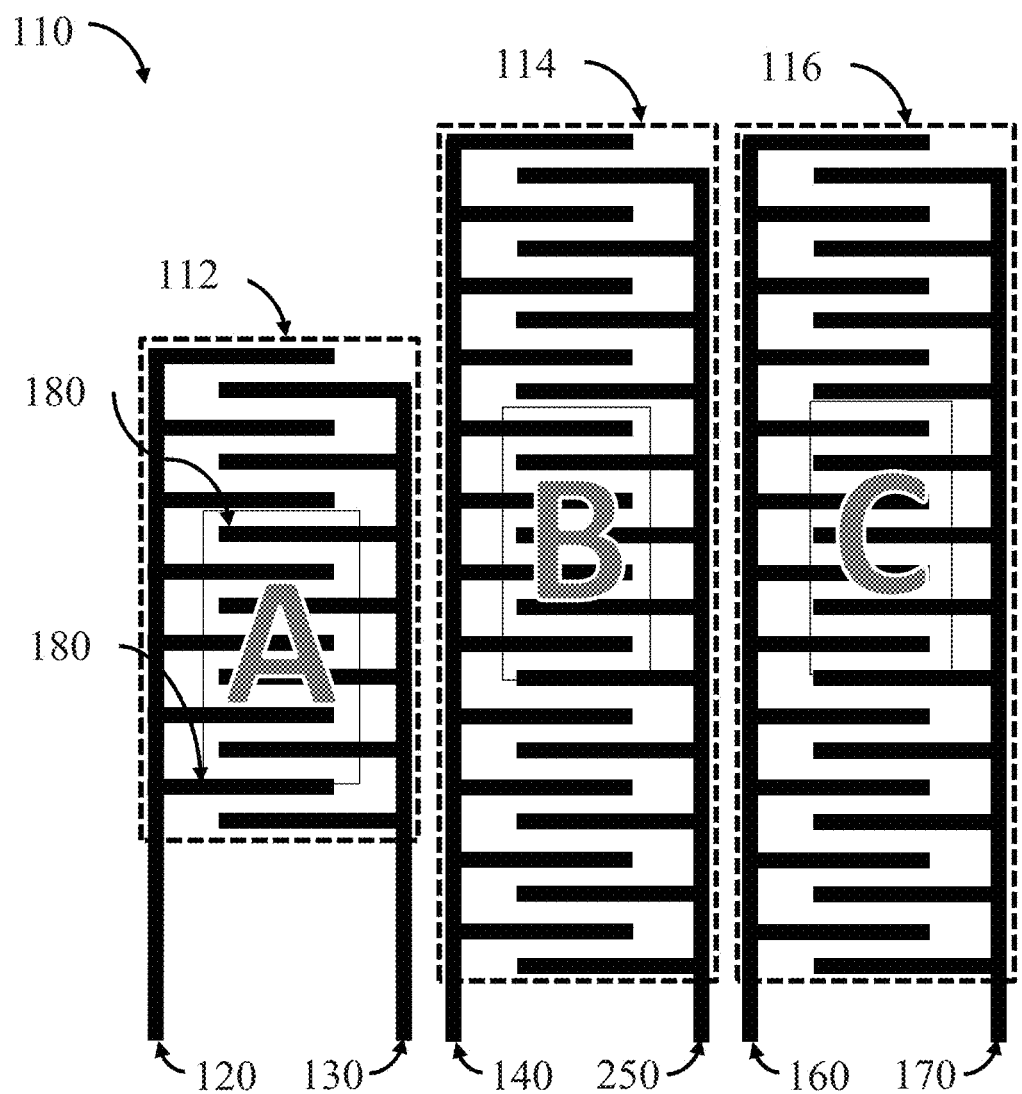
FIGS. 2-6 are illustrations of embodiments of the conductive lead patterns on a sensor pad.
Figure 3:
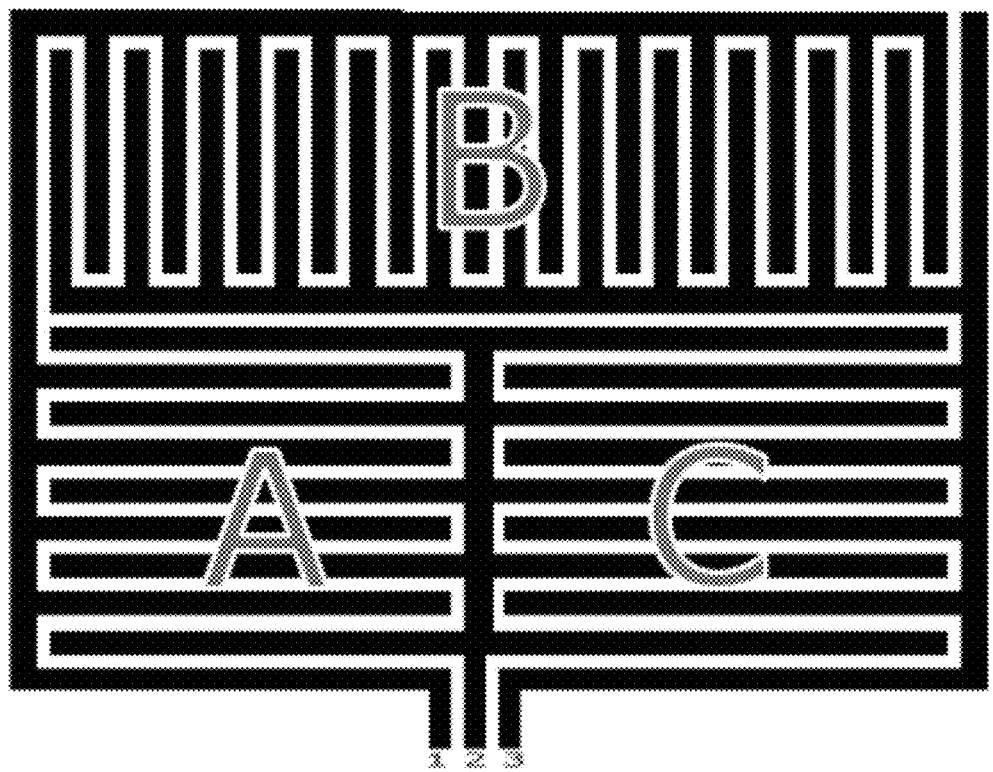

For example, to achieve a three-zone sensor pad, one embodiment might be configured to utilize the equivalent of three adjacent single zones. As shown in FIG. 2, conductive pattern (210) comprises three zones, zone "A" (212), zone "B" (214, and zone "C" (216), each zone comprising two conductive leads (220/230, 240/250, 260/270). As no conductive lead is used in more than one zone, these are effectively three single zone patterns located adjacent to each other. However, FIG. 3 depicts a three-lead, three-zone sensor pad. Note that 3*(3−1)/2=3 zones, and there are equal number of zones and leads. In FIG. 3, zone A is comprised of interdigitated portions of conductive leads 1 and 2, zone B is comprised of interdigitated portions of conductive leads 1 and 3, and zone C is comprised of interdigitated portions of conductive leads 2 and 3.

It should also be noted that in this pattern, Zone A and Zone C are approximately equal in height and width, while Zone B has a different height and width. However, all three zones cover substantially the same area. Conversely, in FIG. 2, one zone (212) has a smaller area than the other two zones (214, 216). In one embodiment, the area of each zone is within 50% of the mean area of all zones. In a preferred embodiment, the area of each zone is within 25% of the mean area of all zones. In a more preferred embodiment, the area of each zone is within 10% of the mean area of all zones. In an even more preferred embodiment, the area of each zone is equal to the area of all other zones.

In these embodiments, the fingers (280) within each zone are approximately the same size. However, other embodiments, including but not limited to those zones defining a trapezoidal or circular shaped area, may have fingers of varying sizes. In one embodiment, the size of each finger in a zone is within 50% of the mean size of all fingers in the zone. In a preferred embodiment, the size of each finger in a zone is within 25% of the mean size of all fingers in the zone. In a more preferred embodiment, the size of each finger in a zone is within 10% of the mean size of all fingers in the zone. In an even more preferred embodiment, the size of each finger in a zone is equal to the size of all other fingers in the zone.

Figure 4:
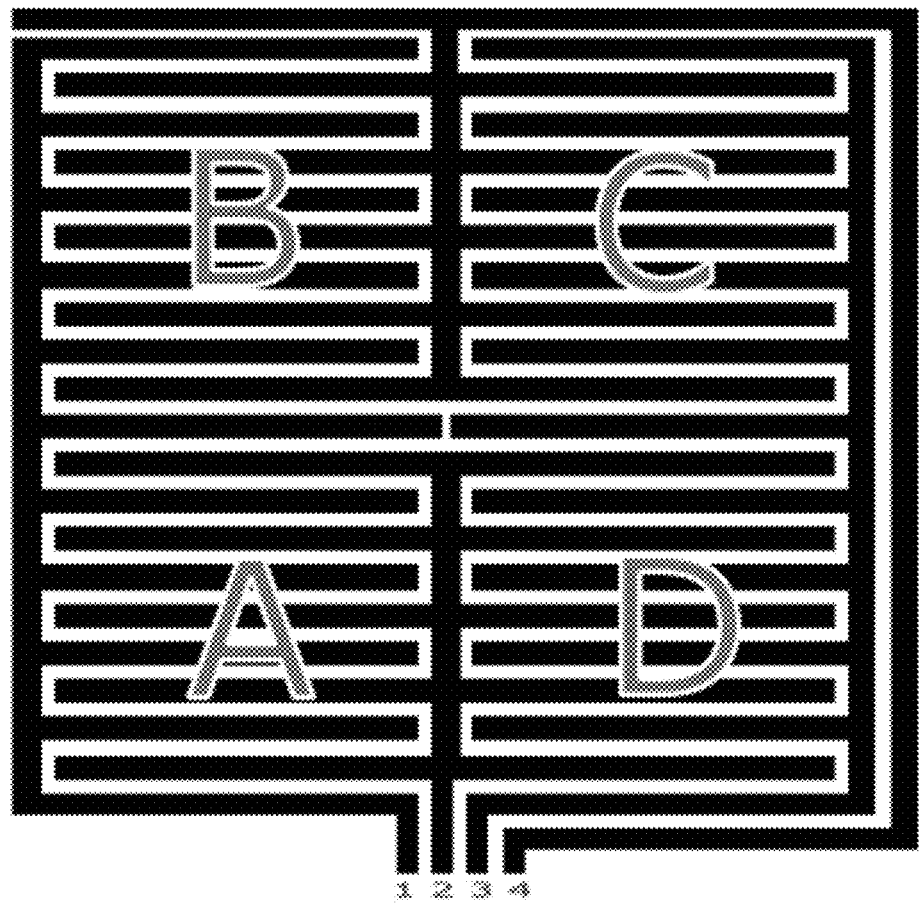
Figure 5:
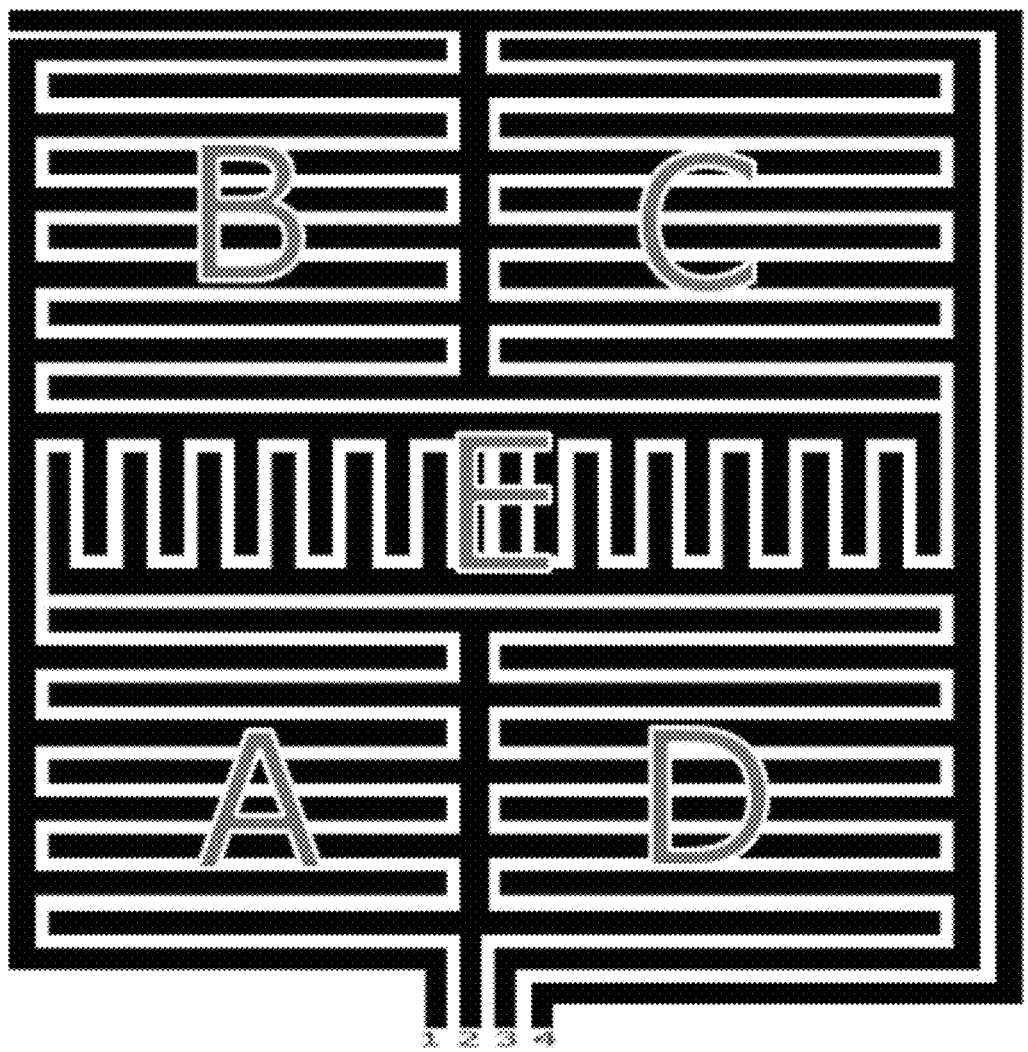
Figure 6:
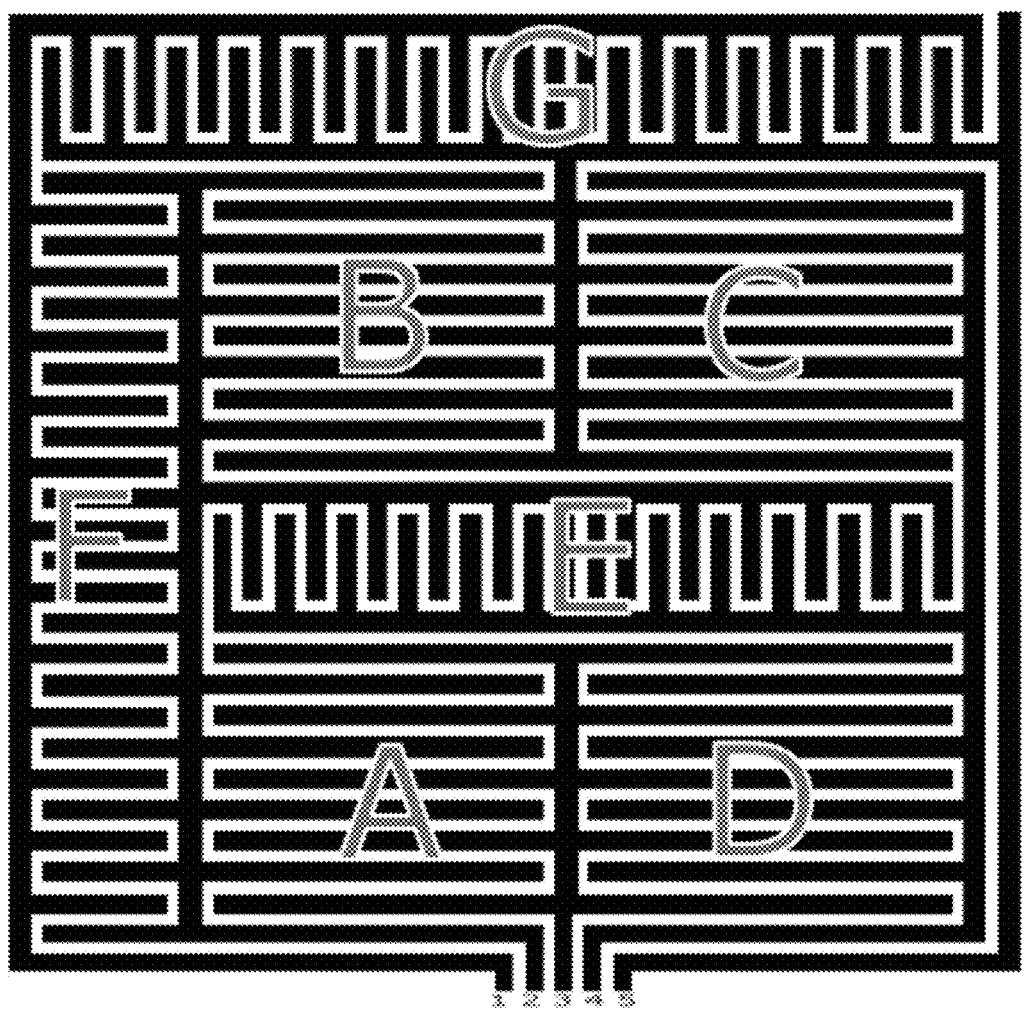

FIG. 2 depicts a 3 zone, 6 lead pattern, with zones A and B having equal areas and dimensions, and zone C having a different area and different dimensions. FIG. 3 depicts a 3 zone, 3 lead pattern, with zones A and B having equal areas and dimensions, and zone C having a similar area with different dimensions. FIG. 4 illustrates one embodiment of a 4 zone, 4 lead pattern, with zones of equal areas and dimensions. FIG. 5 illustrates one embodiment of a 5 zone, 4 lead pattern, where zones A-D are of equal area and dimensions, while zone E has an equivalent area with different dimensions. And FIG. 6 depicts one embodiment of a 7 zone, 5 lead pattern.

Figure 7:
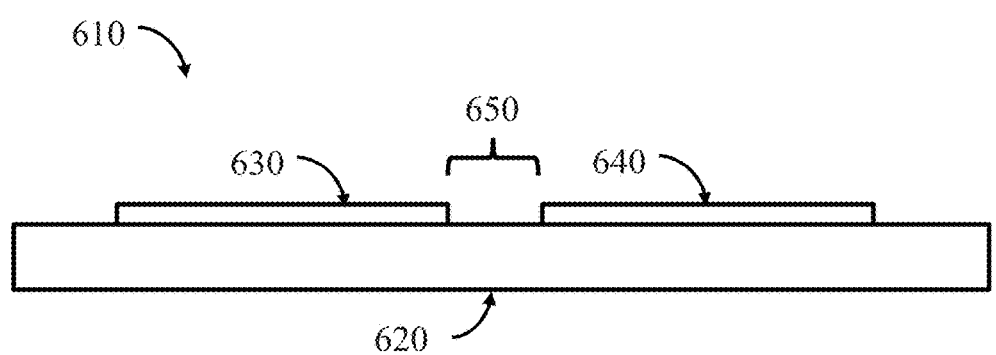
FIGS. 7 and 8 are side-view illustrations of embodiments of sensor pad configurations.

Referring to FIG. 7, one embodiment of a sensor pad comprises a substrate (620), for example, a polymer film such as silicone or polyethylene terephthalate (PET), where a conductive layer is deposited on a surface of the substrate and conductive leads (630, 640) are patterned via etching. Note that the distance (650) between the conductive leads (630, 640) is generally small. When the sensor pad is deformed, such as when an individual is sitting or lying on the pad, the distance (650) may change. Changes in distance cause changes in impedance values. Minimizing those changes in impedance values when the pad is deformed is preferred. In preferred embodiments, the device is configured such that the combined thickness of the substrate and conductive leads is smaller than the distance between the conductive leads. In a more preferred embodiment, the combined thickness is less than 1/10 the distance between the conductive leads. In a still more preferred embodiment, the combined thickness is less than 1/20 the distance between the conductive leads.

In one exemplary embodiment, a 10 micron layer of aluminum was deposited on a 38 micron PET substrate. The aluminum layer was acid-etched to create the digitized pattern with 1 mm spacing between the conductive leads. In this configuration, the ratio (0.048 mm/1 mm) allows the sensor pad to generally deform without meaningful changes in the spacing and thus avoids any meaningful distortion effect.

Figure 8:
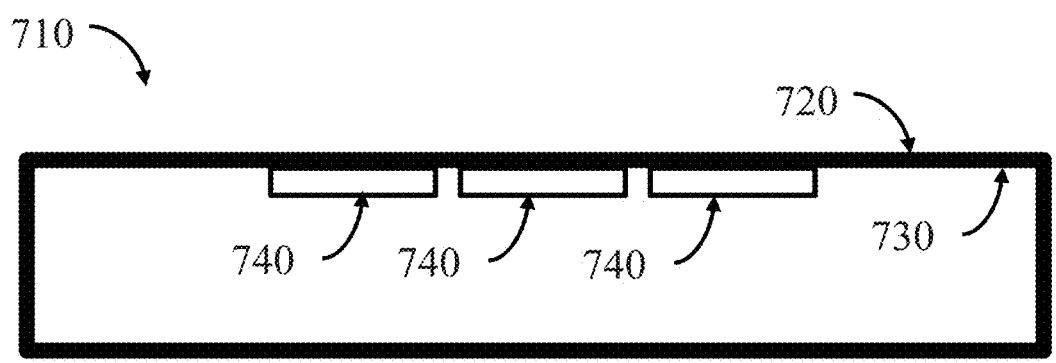

While some embodiments have exposed conductive leads on an outer surface of a substrate, other embodiments have hidden or unexposed conductive leads located on an interior (or otherwise out of sight) surface of a product. Referring to FIG. 8, one alternate embodiment of a sensor pad (710)—for example, part of a mattress or chair cushion—is illustrated as having a top layer (720) having an inner surface (730). The top layer may include single or multiple layers of single or multiple materials. For example, the top layer could be the outer layer of a mattress, or the covering of a chair cushion. Conductive leads (740) are deposited on the inner surface (730). Alternatively, in cases such as wheelchairs, the conductive leads can be deposited onto the underside of the seating platform. In other alternatives, the conductive leads are deposited on the outer or upper surface of such products (e.g., cushions, mattresses, wheelchair seats). In still other alternatives, the conductive leads are deposited on the interior or exterior facing surface of a layer of an incontinence pad, preferably the backsheet or barrier layer.

Typically, the sensor pad will not be exposed directly to biofluids or other forms of moisture, although that is not a requirement. The sensor pad, and specifically the conductive leads, will often be separated from the source of moisture by at least one substrate. These substrates may include almost any material, including but not limited to absorbent articles such as bedsheets, incontinence pads, diapers, and articles of clothing, as well as non-absorbent materials, such as polymer films.

Figure 9:
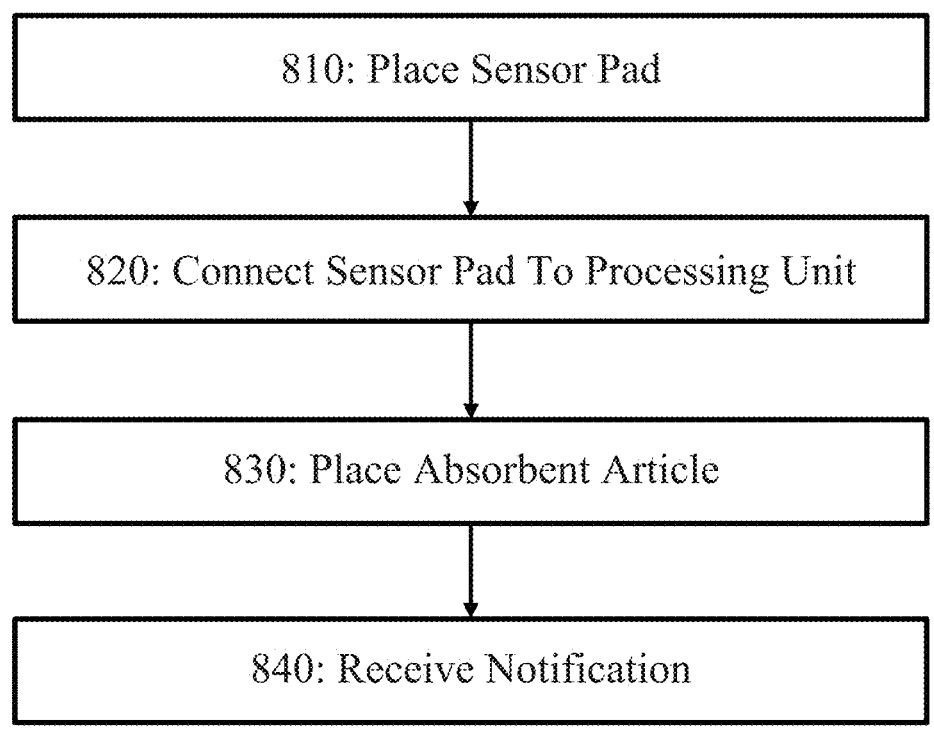
FIG. 9 is a flowchart describing an embodiment of a process for using a moisture detection system.

Referring to FIG. 9, a caregiver could place a sensor pad (810) in a location at least partially covering the location where a biofluid may be discharged, such as on the seat of a hospital wheelchair. The caregiver could then connect the sensor pad to the processing unit (820), typically either via a wired or wireless connection. The caregiver might then place a substrate (830), including but not limited to an incontinence pad, over the sensor pad, and an individual, perhaps in a hospital gown, would sit on the incontinence pad located over the sensor pad. In preferred embodiments, the nurse or other caregiver would be notified (840), e.g., via email, text message, or some alert mechanism that a moisture event was detected. After a moisture event occurs, the caregiver can discard the used substrate (e.g., the incontinence pad) without discarding the sensor pad.

Figure 10:
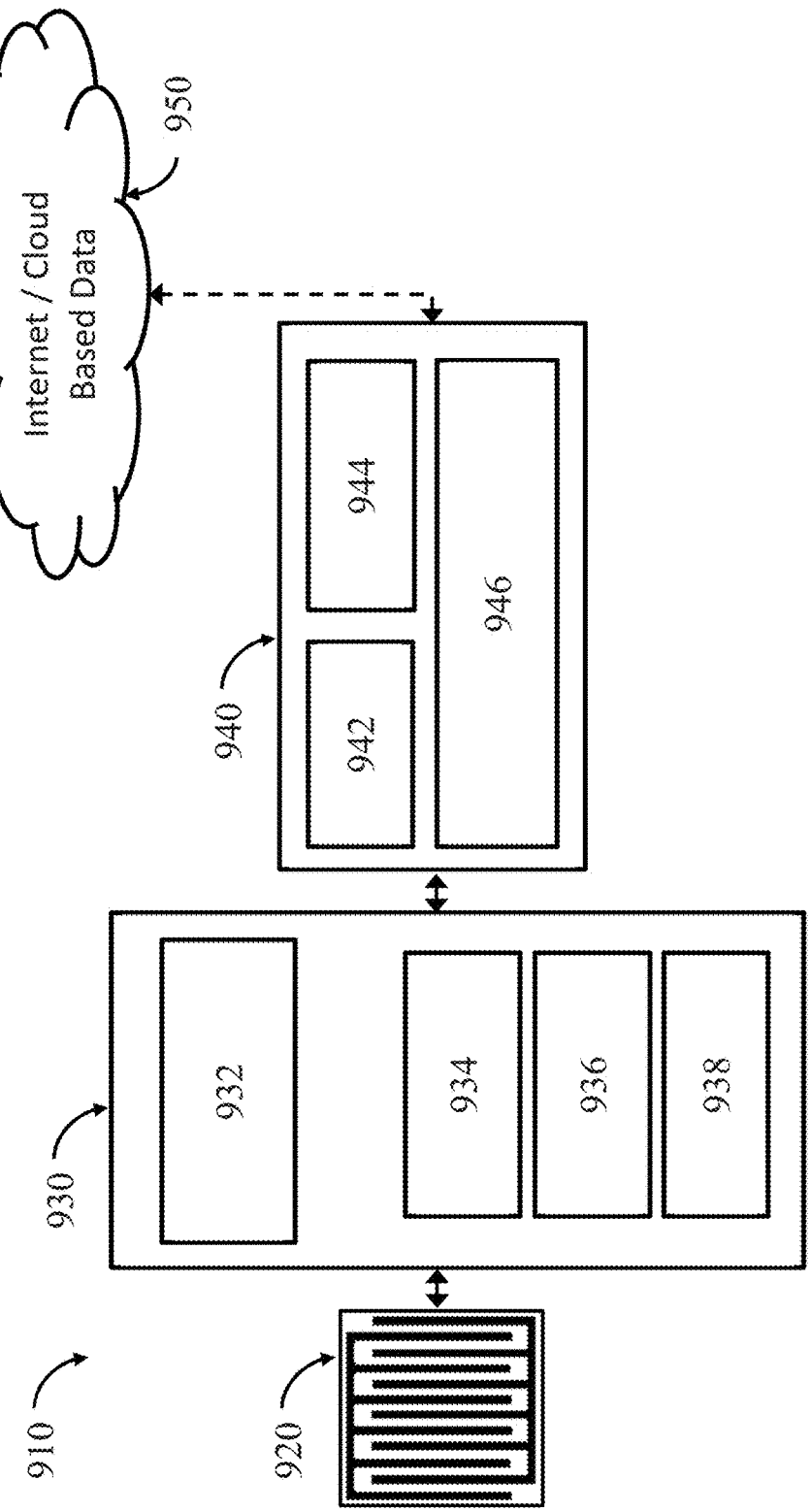
FIG. 10 is an illustration of an embodiment of a moisture detection system.

FIG. 10 refers to an embodiment of the moisture detection system (910). At least two of the conductive leads on the sensor pad (920) connect with coupling unit (930). The coupling unit typically is contained a separate housing (not shown), and comprises an impedance signal acquisition unit (932) for reading or otherwise capturing the impedance signal from the sensor pad. This can include a direct digital synthesizer (DDS) or other device as known to those skilled in the art. The coupling unit may also comprise at least one sensor (934, 936, 938). Many variations and combinations of sensors are envisioned, including but not limited to accelerometers, humidity sensors, and temperature sensors.

Figure 11:
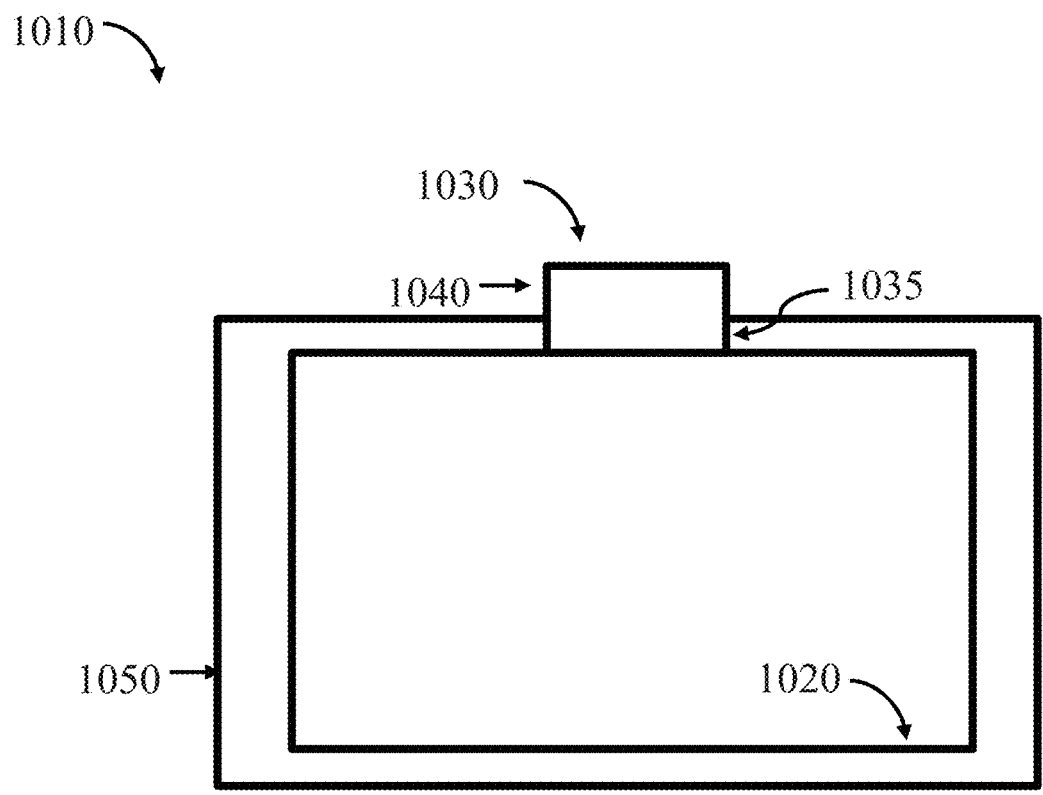
FIGS. 11 and 12 are illustrations of embodiments of placement of a sensor pad.
Figure 12:
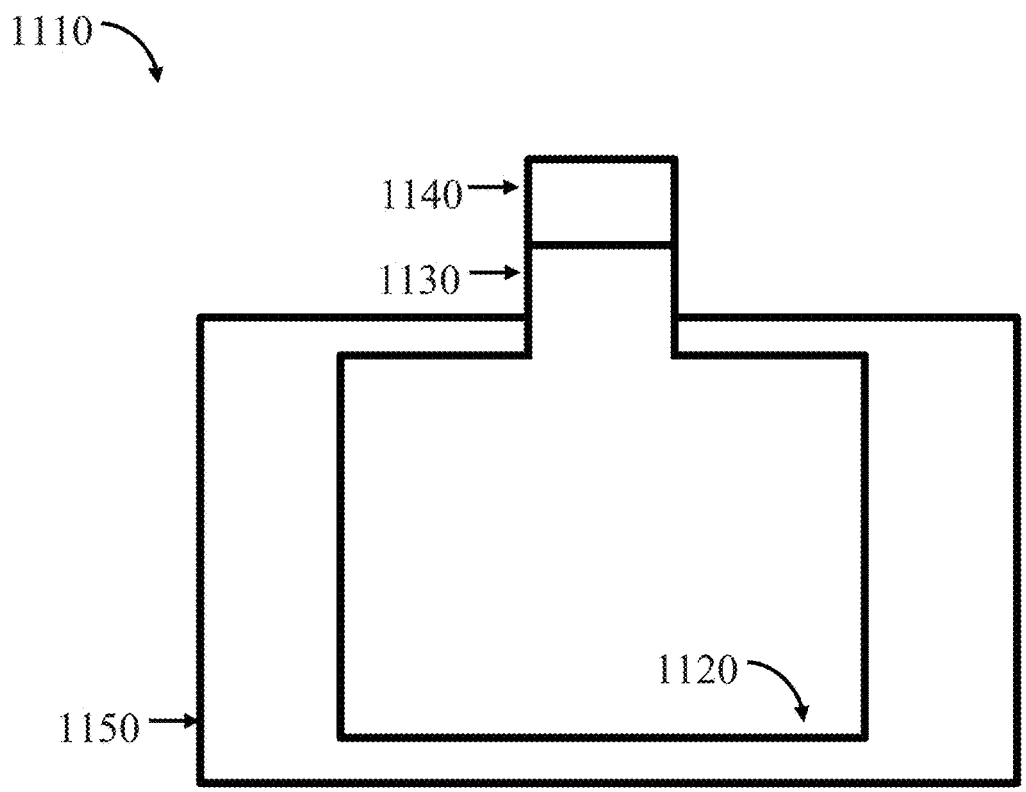

Often, there is a need or desire to prevent individuals from pressing against hard, raised or uneven objects, such as plastic housing for a coupling unit. In these instances, the sensor pad can be configured such that a coupling unit is attachable to a patient support structure at or substantially at an edge of the patient support structure. As shown in FIG. 11, some embodiments (1010) are envisioned whereby the sensor pad (1020) is connected to the coupling unit (1030), such that a portion (1035) of the coupling unit remains on the top of the patient support structure, while another portion (1040) "hangs" over the edge of a support structure (1050). In a preferred embodiment, shown in FIG. 12, sensor pad (1120) is configured such that a portion (1130) of the sensor pad "hangs" over the edge of a support structure (1150). In this embodiment, no portion of the coupling unit (1140) is on the top surface of the support structure (1150).

The accelerometers may perform several functions, by themselves or in conjunction with other sensors. For example, in one embodiment, any non-zero acceleration indicates an individual is moving and is therefore alive. In some embodiments, acceleration detected above a predetermined threshold indicates that any change or fluctuation in measured impedance may be due to motion, and the readings should be discarded or otherwise not considered when detecting moisture until the acceleration is reduced. In still other embodiments, acceleration above a predetermined threshold prevents impedance values from being measured at all during the period of motion.

Further, the accelerometer, or the accelerometer in conjunction with a gyroscope, may be used to detect or estimate respiratory rates. Human respiratory rates vary by age, but are typically between 12 and 50 breaths per minute. A wide range of sampling rates may be utilized, but a preferred embodiment has a sampling rate ranging between around 1 Hz up to 100 Hz. The data can be analyzed immediately, or sent to a database for analysis at some time in the future.

It is envisioned that in arrangements where the coupling unit comprises an accelerometer, the system can be configured to determine at least one of an individual's respiratory rate, body position, movement pattern, or sleeping pattern based on data from the accelerometer.

Referring back to FIG. 1, the embodiment of the moisture detection system also comprises a processing unit (50) configured to read impedances of the sensor pad, the processing unit comprising a controller (52) and a communication interface (54). In this particular embodiment, the processing unit is connected to the coupling unit via an optional cable (40), although embodiments with other connections, including wireless connections, are envisioned. The processing unit may comprise other components or units not shown in FIG. 1, including but not limited to status light(s), a display unit, memory, a speaker or tone generator, a touchpad, or outputs for storage devices. In some embodiments, the processing unit also controls power for the processing unit and sensor pad. This may occur in a variety of ways, including but not limited to plugging the processing unit into an A/C wall outlet or connecting to a battery pack.

FIG. 1 also depicts a processing unit comprising an optional signal analysis unit (56) in the processing unit (50). A signal analysis unit is a device or component capable of measuring impedance characteristics, including but not limited to network analyzers, complex impedance meters, capacitance meters, inductance meters, and ohmmeters.

FIG. 1 further depicts a server, database, or other device (70). In this embodiment, a communications interface (54) is connecting directly to the server, database, or other device directly through a wireless signal, although other configurations are envisioned, including but not limited to connecting wirelessly through a mesh network, or connected through a wired connection.

FIG. 10 shows a similar embodiment, where the processing unit (940) communicates with the coupling unit (930) and provides output to an internet or cloud-based operation (950). The processing unit comprises a controller (942), a signal analysis unit (944), and a communication interface (946). In this embodiment, the signal analysis unit is located in the processing unit, although other configurations are envisioned, such as in a housing located apart from the processing unit.

The moisture detection system operates by measuring impedance with the conductive leads of the sensor pad. This does not require contact with moisture—each zone is able to measure impedance in some volume of space above the zone, the dimensions of which are generally controlled by the sensor pad configuration and the power utilization. As individuals or additional moisture are introduced into the volume of space being measured, the impedance values change as compared to a reference or baseline value.

Figure 13:
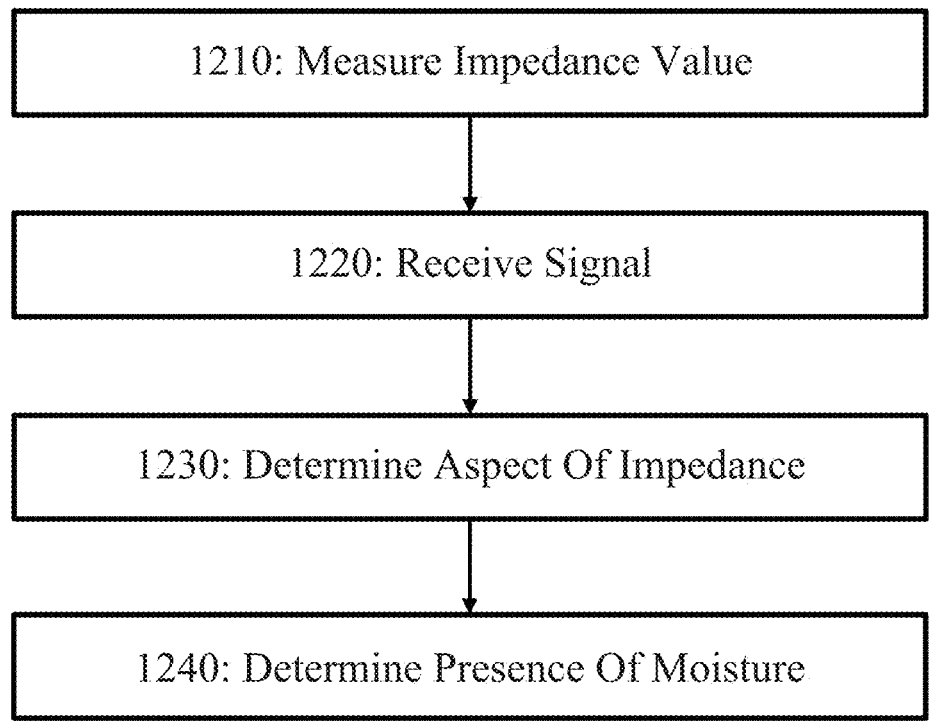
FIG. 13 is a flowchart describing an embodiment of a process for using a moisture detection system.
Figure 14A:
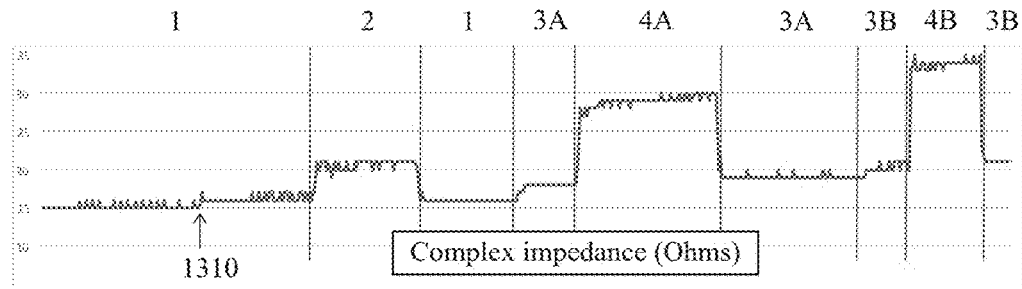
FIGS. 14A-D are graphs of data collected using an embodiment of a moisture detection system.
Figure 14B:
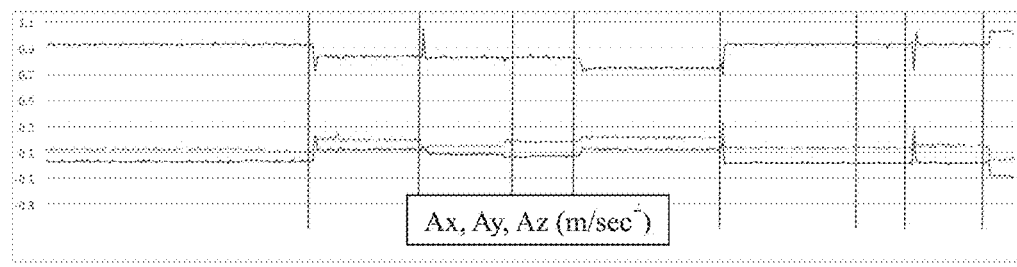
Figure 14C:
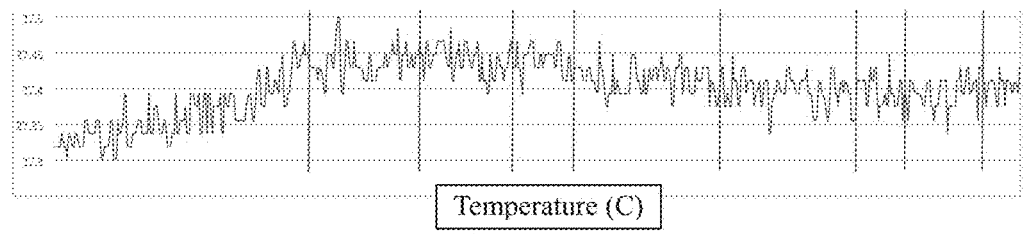
Figure 14D:
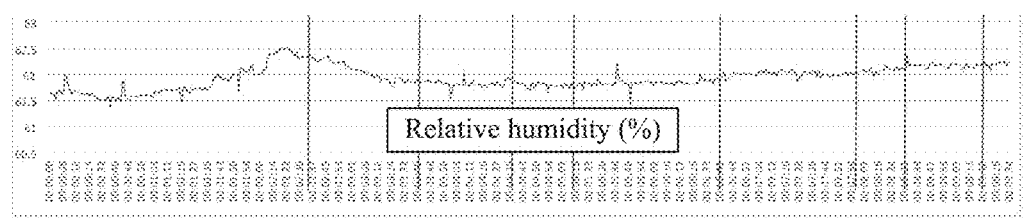

Referring to FIG. 13, these impedances are measured (1210) by an impedance signal acquisition unit. A signal representative of the measured impedance value is sent to a processing unit. The processing unit receives the signal (1220), and either analyzes the signal itself, or sends the signal on to a server, database, or other device for analysis.

Impedance describes a measure of opposition to alternating current and is described by a complex number. The real part of impedance describes the resistance (amplitude ratio of voltage and current), and the imaginary part describes the phase differences. Phase differences only occur when the circuit has a capacitive or inductive component, and typically a plus sign is used to indicate the inductance of the imaginary part and a negative sign is used to indicate the capacitance of the imaginary part.

If an accelerometer is present in the system, a threshold value can be determined whereby the detection of moisture, as indicated by the impedance values read from the sensor, is determined to be inaccurate. For example, if an impedance reading is taken when the accelerometer is indicating very little movement by the person being monitored, then the resulting determination of the presence of moisture is probably accurate. However, if the person is moving vigorously and the sensor pad is thus deforming, then the measured impedance values may be less accurate for determining the presence of moisture. Numerous options for handling the impedance readings are envisioned. In certain embodiments, the impedance readings during times of vigorous motion by the person being monitored are simply discarded. In other embodiments, the sensor readings are recorded for diagnostic purposes, but no moisture determination is made. And in still other embodiments, the sensor controller tells the sensor not to record additional readings for a certain time period, or until the accelerometer reading falls below a threshold value.

If the processing unit analyzes the signal, the signal analysis unit within the processing unit will generally determine at least one aspect of the measured impedance (1230), which include but are not limited to: the maximum frequency of the real part of the complex impedance (Fp), zero-reactance frequency (Fz), magnitude of the real part of the complex impedance (Zp), resonant frequency of the imaginary part of the complex impedance (F1), signal magnitude at the resonant frequency of the imaginary part of the complex impedance (Z1), antiresonant frequency of the imaginary part of the complex impedance (F2), and signal magnitude at the antiresonant frequency of the imaginary part of the complex impedance (Z2). Typically this is done be measuring multiple frequencies across the sensor pad and using multivariate analysis to analyze the multivariable response.

In some embodiments, a controller in the processing unit controls the sensor pad's functionality, including the sample rates and frequency ranges. In some embodiments, the sampling rate of the sensor pad may be held constant; in other embodiments, the sampling rate may vary based on conditions. For example, while a baby remains relatively motionless in a crib, the sampling rate may be 1 Hz. When the baby begins moving, the sampling rate may reduced.

Alternatively, for diagnostic purposes, it may be of benefit to increase the sampling rate when an increase in moisture is detected (e.g., when a person is urinating or defecating) and to decrease it at other times.

Once the signal analysis unit has determined at least one aspect of a real and imaginary impedance, the processing unit can either make a determination whether moisture is present (1240), or send a signal representative of the at least one aspect to a server, database, or other device where the determination can be made (1240).

It is envisioned that many algorithms can be utilized for determining whether a moisture event has occurred. However, in general the presence of moisture is based on a function of at least one of a threshold and at least one aspect of the first real and/or imaginary impedance.

Figure 15:
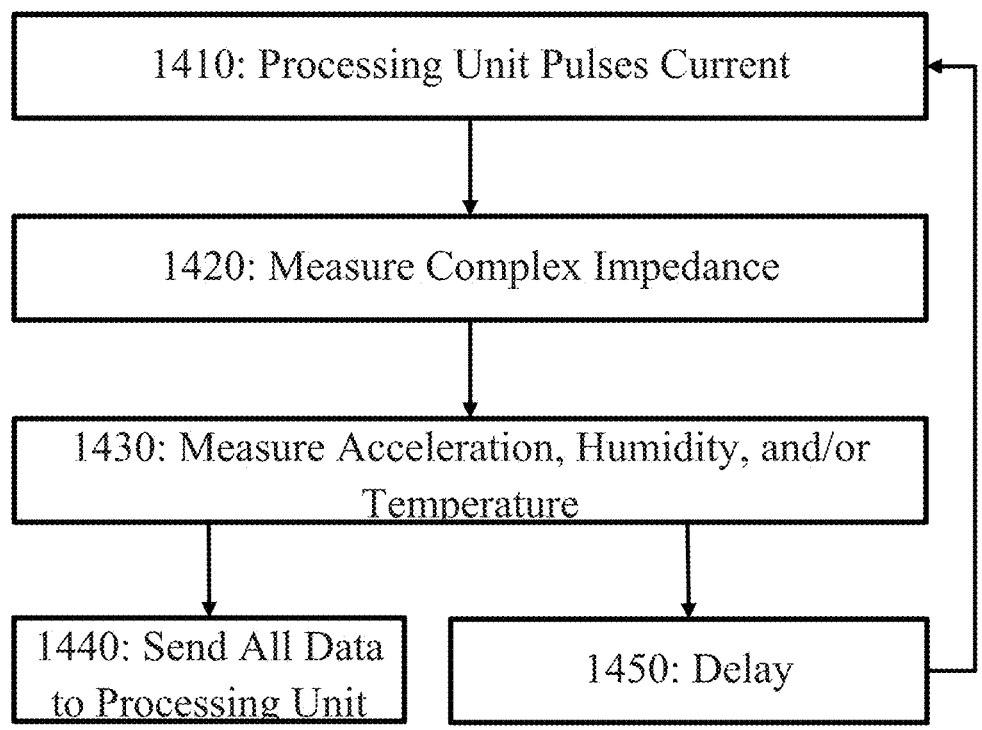
FIG. 15 is a flowchart describing an embodiment of a process for gathering data with a moisture detection system.

One example of the algorithm can be described with reference to FIGS. 14-16. FIGS. 14A-D demonstrate the determination of four distinct states of moisture, (i) no person present-no moisture present (State "1"), (ii) person present-no moisture present (State "2"); (iii) no person-moisture present (State "3A" or "3B" depending on the volume of moisture, as described below), and (iv) person-present-moisture present (State "4A" or "4B"), over a 9 minute, 35 second (00:09:35) period by one embodiment of the moisture detection system. This embodiment was installed on a standard commercial bed and used a single-zone sensor pad (comprised of etched aluminum on PET in this embodiment) placed on top of the mattress and under the bed sheet. At 00:01:30 in this example, a disposable incontinence pad (Medline Extrasorbs AP 30"×36") was placed on the bed sheet directly above the sensor pad. The sensor pad and its coupling unit were connected to a wall-mounted processing unit via a Category 6 (Cath) cable.

Generally, the sensor pad functions by applying an AC electric current through the sensor pad, across a chosen pair of leads. Once this occurs, an electromagnetic field is established, and the pad effectively becomes an antenna. As such, the sensor now has a complex impedance associated with it, which can be observed at a single frequency (for example, at 5 MHz) or over a range (for example, 4 MHz to 6 MHz). The electromagnetic field around the sensor is altered by ambient conditions, including but not limited to the presence of moisture. For example, if a wet surface is in close enough proximity to the sensor, it will affect the capacitive and inductive aspects of the impedance. If a wet surface comes in contact with the sensor, it will affect the resistive aspect of the impedance. The flowchart of FIG. 15 illustrates how the sensor pad functions in this example. Here, the processing unit pulses an 80 micro amp current at 5.3 MHz frequency to the sensor pad for 50 microseconds (1410) at one-second intervals (1450) and then measures the resulting complex impedance (in Ohms) generated in the sensor pad (1420). In addition, the coupling unit contains an accelerometer, temperature sensor and humidity sensor, which generated, respectively, three-dimensional acceleration (in meters/second), temperature (in degrees Celsius) and relative humidity (as % of saturation level) measurements (1430) at one-second intervals (1450). The measurements were relayed to the processing unit (1440). In this example, the processing unit continuously relayed all of the received data over the internet to a server, where the data were recorded and processed using one version of a software algorithm to determine the state of moisture.

Figure 16:
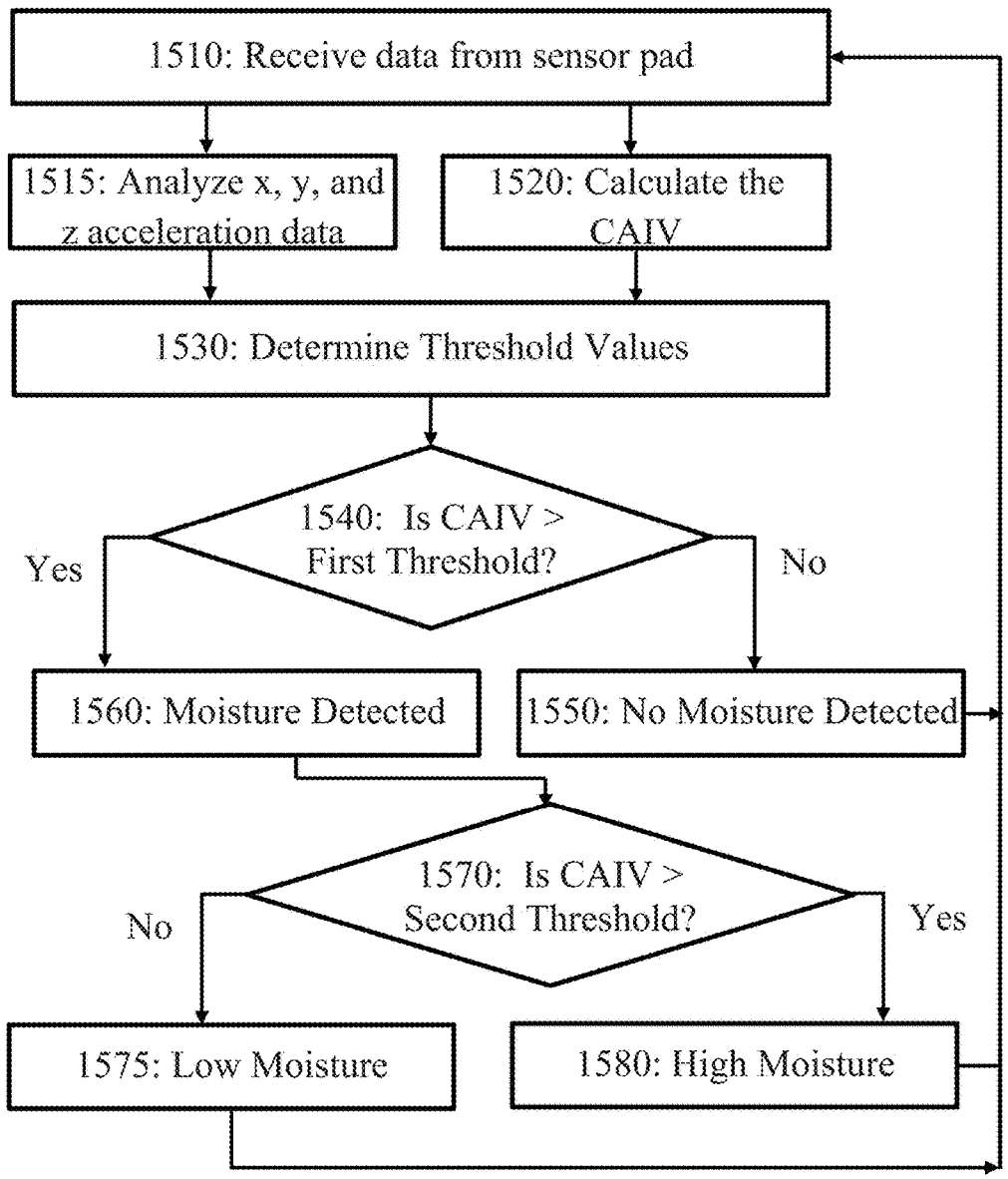
FIG. 16 is a flowchart describing an embodiment of a process for analyzing data with a moisture detection system.

The algorithm in this example is illustrated in FIG. 16, and functions as follows:

Subsection A. Once data starts to be received from the sensor pad (1510), the algorithm first determines if a person is present by analyzing the x, y and z acceleration data for motion patterns indicative of a human presence (1515). Specifically, the algorithm continuously calculates (i) the change in each of the x, y and z acceleration values from their immediately preceding value (the "acceleration change value") and (ii) the number of times any of the acceleration change values exceed 0.005 meters/second$^2$ over the preceding 30-second period. If the number of times is fewer than 30 (out of a maximum of 90, i.e., 30 seconds×3 changes calculated each second), the algorithm determines no person is present; if it is more than 40, the algorithm determines that a person is present; if it is between 30 and 40 times, the algorithm makes an inconclusive determination and repeats the analysis on the next rolling 30-second interval, until it is able to make a conclusive determination. In this example, the acceleration change values exceeded 0.005 meters/second$^2$ only 25 times in the first 30 seconds of operation, so the algorithm made the "no person present" determination. (Note that, even with no person present, small random variation in x, y and z acceleration data still do occur due to ambient environmental vibration and air movement. Note further that the algorithm is programmed to send an alert to the system operator if it cannot make a determination of person present/not present after 3 minutes.) Concurrent with determining the presence of a person, the algorithm calculates the average of the last 20 measured impedance values (1520) (i.e., over the preceding 20 second interval). This is the "current average impedance value" or "CAIV". The algorithm determines if moisture was present in the incontinence pad above it by comparing the CAIV to a calculated threshold value. Based on inputs of (i) no person present, (ii) a temperature (~27 C) within a 25-30 C degree range, (iii) relative humidity (61-63%) within a 60-65% range and (iv) the use of a Medline Extrasorbs AP incontinence pad, the algorithm utilizes previously stored data to determine or extrapolate various threshold values. In this example, it determined (1530) that a 17 Ohm threshold value for the presence of moisture (the "first threshold value") when no person is present is appropriate. Here, a lookup table was utilized, with data representing previously recorded sensor pad measurements at a variety of conditions stored in a database. However, other methods for determining or extrapolating the threshold values, including but not limited to utilizing an equation representing a fitted curve, are envisioned. The CAIV is then compared to the threshold values (1540). For any CAIV above the first threshold value, the algorithm would deem moisture to be present (1560) and would run additional tests to approximate the volume of moisture (as detailed in subsections D, E, G, and H below); for any CAIV below the first threshold value, moisture would be deemed not present (1550). During the first 00:02:39 of this example, the CAIV was always below the first threshold value. Thus in this example, the algorithm determined that no person and no moisture was present and designated this period as State 1. Note in FIG. 14 that placing an incontinence pad on the bed (1310) at 00:01:30 changed the impedance value slightly (~7%), however, it did not elevate the CAIV above the first threshold value. Note further that the algorithm recorded the most recent CAIV during State 1 as its "State 1 reference value" for use in subsequent analytics, as detailed below.

Subsection B. At 00:02:39, a test subject (a 35 year-old, 180 pound, healthy male) reclined on the bed on his dorsal side, with his buttocks centered on top of the incontinence pad. At approximately 00:02:52, the algorithm detected that the acceleration change values had exceeded 0.005 meters/second$^2$ 41 times over the preceding 30 second period and thus made the determination of "person present" (following the logic pattern described in subsection A, above). To determine when the change took place, the algorithm then looked for any instances in which the acceleration change values exceeded 0.03 meters/second$^2$ over the preceding 30 seconds, as this degree of movement is indicative of an person getting into or getting out of a bed. The algorithm detected that each of the x, y and z acceleration change values exceeded this threshold at 00:02:39 and thus determined that the change from "person not present" to "person present" occurred then. (Note that if the algorithm does not find any instances that exceed this 0.03 meters/second$^2$ threshold, it assumes that the actual change to "person present" happened 15 seconds prior to the time at which the "40 times" threshold was reached. Upon determining "person present", the algorithm uses a different means to determine the presence of moisture. First, because significant subject motion, such as changing positions on the bed, getting on or off the bed, or coughing can impact the measured impedance, the algorithm requires a 20 second interval in which none of the x, y or z-acceleration values change more than 0.025 from their immediately preceding values (a "motion-stable interval") for its calculation of the CAIV. In this example, motion-stable intervals began at approximately 00:03:13, at which point the algorithm began generating CAIVs again. Then, with a person present, the algorithm compared the CAIV to the State 1 reference value, which in this example was from the period from 00:02:19 to 00:02:39, i.e., the last full 20 second interval before the presence of a person was detected. In making this comparison, the algorithm confirmed that temperature and relative humidity were in the same range as when the State 1 reference value was generated (that was the case in this example; if it were not, the algorithm would make proportional adjustments). The algorithm determined that any CAIV less than 150% of the State 1 reference value indicated that no moisture is present when a person's presence was detected (1530). That was the case in this example: the CAIV at 00:03:13 was 20.5 Ohms, the State 1 reference value was 16.3 Ohms, and 20.5±16.3=126%, which is less than the 150% threshold. The CAIV±State 1 reference value continued to be less than 150% until the subject left the bed at approximately 00:03:45. Thus, the algorithm classified the period from 00:02:39 (which a person was first detected as present) to 00:03:45 as State 2.

Subsection C. At 00:03:45, the subject left the bed. By 00:04:10, using the logic pattern detailed in subsection A (i.e., the total number of acceleration change values>0.005 meters/second during the preceding 30-second period), the algorithm determined "person not present", and then, using the logic pattern detailed in subsection B (i.e., when acceleration change values exceeded 0.03 meters/second over the preceding 30 seconds), it determined that the change from "person present" to "person not present" occurred at 00:03:45. Upon making this determination, the algorithm following the logic pattern as detailed in subsection A to determine "no moisture present" (i.e., CAIVs below the first threshold value), and it classified the interval beginning at 00:03:45 as State 1.

Subsection D. At 00:04:40, approximately 40 ml of simulated urine (a saline solution) was deposited onto the incontinence pad, which caused the measured impedance value to increase from 16 to 18 Ohms over the following 8 seconds. The algorithm, still not detecting acceleration change values above the threshold as described in subsection A, continued to follow the logic steps as detailed in subsection A for determining the presence of moisture. Beginning at approximately 00:05:08, the CAIV exceeded the first threshold value. The algorithm then compared the value to a "second threshold value" (1570), which is determined to be 20 Ohms as described in subsection A (1530) given the observed temperature and relative humidity rates and the type of incontinence pad used in this example. Because the CAIVs beginning at 00:05:08 exceeded the first threshold value but did not exceed the second threshold value, the algorithm deemed a "25-50 ml moisture event" to have occurred (1575). Finally, the algorithm observed the time at which the measured impedance value first began to increase, which it determined as 00:04:40. The algorithm considered this point of first increase to be the beginning of a new state, and it thus designated the interval beginning at 00:04:40 as State 3A (The "A" indicative of the volume of moisture). Further, the algorithm retained the last full 20 interval before impedance values began to increase, i.e., 00:04:20 to 00:04:40, as the State 1 reference value (16.0 Ohms).

Subsection E. At 00:05:18, the same subject as above again reclined on the bed in the same position. Following the logic pattern as described in subsection B, the algorithm determined "person present" beginning at that time and began comparing CAIVs to the State 1 threshold value retained in memory. At 00:05:42, the CAIV was 178% of the State 1 reference value. Because this value exceeded the 150% threshold (as described in subsection B above) but was less than a 200% threshold (1570), the algorithm determined a "25-50 ml moisture event" to have occurred (1575). The algorithm observed the time at which the measured impedance value first began to increase, which it determined as 00:05:19 and considered this point of first increase to be the beginning of a new State 4A.

Subsection F. At 00:06:40, the subject left the bed again. Following the logic patterns as described in subsections D and E, the algorithm determined "person not present" and "moisture present" beginning at that time, and thus classified the period beginning at 00:06:40 as State 3A.

Subsection G. At 00:08:03, an additional 40 ml of simulated urine was deposited onto the incontinence pad, and the measured impedance value increased to between 20 and 21 over the next 6 seconds. The algorithm continued to follow the logic pattern as described in subsection G. However, at 00:08:27, the CAIV began to exceed the second threshold value (1570) (20 Ohms). Thus, the algorithm determined a "50-100 ml moisture event" to have occurred (1580), and it classified the interval beginning at 00:08:03 as State 3B.

Subsection H. At 00:08:33, the same subject as above again reclined on the bed in the same position. The algorithm followed the logic steps as detailed in subsections B and F. By 00:08:52, however, the CAIV was more than 200% of the State 1 reference value (1570). Thus, the algorithm deemed a "50-100 ml moisture event" to have occurred (1580), and it classified the interval beginning at 00:08:33 as State 4B (the "B" indicative of a higher volume moisture event).

Subsection I. At 00:09:20, the subject left the bed for the final time. The algorithm followed the same logic pattern as described in subsection H and classified the interval beginning at 00:09:20 as State 3B. The collection of data in this example stopped at 00:09:35.

Note that the thresholds utilized by the algorithm can be absolute values, or relative values. In the above example, they were set up as absolute values (17 ohms and 20 ohms), but they could also just as easily have been relative values, including but not limited to values such as 110% over the stage 1 reference value, or 3 ohms greater than the stage 1 reference value. Further, note that while only two categories of moisture were identified in this example, one skilled in the art will recognize that additional categories can be utilized simply by adding additional threshold values.

Although not required, adjusting the reference or baseline values to account for ambient conditions can therefore help prevent false positives and false negatives.

The above example used a single sensor pad to estimate the volume of moisture detected. In similar fashion, volume of a moisture event may be determined, estimated, or categorized based on the impedances with a multi-zone sensor pad as well. For example, a "minor" moisture event might only be detected by a single zone, a "moderate" moisture event might be detected by 2 or 3 zones, and a "major" moisture event would be detected by 4 or 5 zones. Alternatively, if a zone on the edge of a conductive pattern (e.g., FIG. 6, Zone "F" or "G"), a "major" moisture event could be triggered—as the risk of the biofluid escaping whatever containment mechanisms are in place may be higher than if a more central zone detects moisture. In another embodiment, the volume of an event can be estimated based on the number of zones detecting a moisture event. For example, in one embodiment of a five-zone pad, if only a single zone detects an event, the volume could be estimated at 15 mL. If two zones detect an event, the volume can be estimated at 30 mL. If three zones detect an event, the volume can be estimated at 50 mL, and four zones would indicate a 100 mL volume. In yet another non-limiting alternative, if two zones sense "25-50 mL" of moisture, and a third zone detects "10-25 mL" of moisture, by summing up the detected ranges, the system can estimate that there is between 60-125 mL of moisture within detection range. Because information about a patient's intake and discharge of fluids can be useful for healthcare providers, this ability to approximate the volume of detected moisture can be a valuable clinical tool.

With multi-zone sensor pads, the aspects of the complex impedance can also be used for determining a person's position or movement on the sensor pad. As discussed, each zone may be configured to determine the presence or non-presence of an individual. For example, if a person is lying down on their back on a bed, with a sensor pad under them that has the pattern shown in FIG. 6, six zones could indicate the presence of an individual (A-F). If the person then rolled onto their right side, for example, an individual might only be detected over zones A, D, and F. If the person then rolled back to their left side, the individual might only be detected over zones B, C, and F. If the person sat up, they might be detected only be zones C, D, and E. And if they sat on the edge of the bed, they might be detected only by zone G. Because remaining in one position for an extended period of time increases a patient's risk of developing a pressure ulcer, the ability to monitor patient position and movement can be a valuable clinical tool. As such, this data can be viewed and analyzed over an extended period of time, and alerts or notifications may be triggered if a patient remains in a single position for more than a predetermined period of time.

Once an event or condition has been determined, a server, database, or other device can send out appropriate notifications. For example, a database might have two tables, one table correlating an individual's name with the processing unit that is in use for monitoring that individual, and another table correlating that individual with other people who need to be notified and their contact information in the event of a moisture event, which may be different from the individuals who need to be notified if the individual attempts to stand up, which may be different from the individuals who need to be notified if the individual's breathing becomes erratic. In this example, the processing unit would be configured to send a unique identification of the processing unit to the server to aid in making the determination of who needs to be notified. Once the appropriate individuals are identified, appropriate alerts or notifications can be sent via any appropriate method, including but not limited to text message, email, or telephone.

Alternatively, a signal can be sent back to the processing unit, where the processing unit can cause a message to be displayed on a display screen, sound an alert or notification tone, or otherwise locally indicate an event has occurred.

The moisture detection system may be utilized in a variety of different environments outside of the healthcare industry, including use with domesticated livestock or pets, buildings, liquid containers and transport, and vehicles.

By placing a sensor pad underneath or embedding the sensor into the flooring of areas where farm animals or zoo animals are quartered, including horse stables, livestock pens, and zoo animal habitats, it is possible to monitor the level of moisture on the floor due to the animals' urine or feces. In these conditions, cleaning and maintenance of the animals' living quarters can be optimized and sanitary conditions for the animals can be ensured. Similarly, by placing the sensor pad underneath an area containing pet litter or bedding—including cat litter boxes, rodent and reptile cages, and dog kennels—pet owners, veterinarians or other pet caregivers can monitor a pet's bodily functions and sanitary conditions. In this manner, a pet's caregiver can be informed if the pet's litter or bedding requires changing or if the pet is exhibiting a normal or abnormal pattern of bodily functions.

With respect to buildings, the presence of moisture inside a building is not only harmful because of the leak itself, but such moisture also leads to the growth of mold. Placing the sensor pad along or embedding the sensor into the exposed or non-exposed surfaces of building elements, including floors, subfloors, floor coverings, ceilings, walls, doors, window frames, beams, rafters, studs, roofing and building paper, can provide early detection capabilities for the build-up of moisture due to leaks, spills and other flooding events. For instance, embedding the sensor in the subfloor of a bathroom or kitchen would be an effective way to monitor for slow leaks from plumbing fixtures or unexposed pipes. Embedded sensors in the ceiling of the top floor of a building or on the roofing felt underneath roofing shingles would provide early detection of roofing leaks. Home and commercial building insurance companies could encourage policyholders to implement such sensors in exchange for reduced premiums. Central alarm monitoring companies could offer such sensors to residential and commercial clients as part of a "smart home" or "smart building" offering.

The system can be used to monitor, detect or determine the level of liquid inside a non-metallic container, vessel, pipe, tubing or other structure that may contain a liquid. The sensor could be applied to the exterior or interior surface of the structure to determine the approximate level of the liquid inside the structure. For instance, it could be used to determine the level of fullness of a portable toilet to optimize service scheduling. Another use would be to detect when a pipe that ordinarily should not be full, such as a sewer or septic line, is filling up, thus indicative of a potential clog. This use could be attractive to home and building insurance companies, central alarm monitoring services, plumbers, septic- and sewer-line maintenance companies, and building restoration services companies as another product or service feature to offer customers. An additional use would be to monitor the fill-level or re-fill rate of a well or a cistern, which could be an attractive product or service feature for plumbers to offer customers.

The system also offers a lot of benefit with respect to vehicles. For example, the system could be embedded in the backrest of ventilated car seats. When the system detects that the seat occupant is sweating, it can automatically activate the seat ventilation system to cool the occupant. Alternatively, the system can be applied to the interior surface of automotive or truck tires to provide real-time detection of water on a driving surface. This detection could be factored into the vehicle's traction control system to optimize vehicle safety. For watercraft, the system can be installed on the interior or exterior surface of the hull or a ship, boat or barge to determine the vessel's draft or submersion level. This could be useful for vessels with frequently changing load levels, such as a commuter ferry, as a safety check for overloading conditions. On airplanes, the system could be applied to the interior or exterior surface of the covering of wings, flaps, ailerons, rudders or other critical flight surfaces of an aircraft for the detection of ice accumulation. The system could also be embedded into the floor of a trucking cargo area, a trucking trailer or a shipping container, or into the base of shipping boxes themselves, to detect the presence of moisture. This could be useful to detect if frozen merchandise is melting or the presence of a leak in the shipping container is exposing the merchandise to adverse environmental conditions.

It should be understood that many variations are possible based on the disclosure herein. Although features and elements are described above in particular combinations, each feature or element can be used alone without the other features and elements or in various combinations with or without other features and elements.

What is claimed is:

1. A moisture or fluid detection system, comprising:
    a sensor pad capable of detecting moisture or fluid that is not in contact with the sensor pad, the sensor pad comprising:
        a first substrate;
        a plurality of conductive leads disposed on the first substrate and defining at least one zone, each zone defined by an area in which one conductive lead is interdigitated with another conductive lead; and
        a coupling unit coupled to at least two conductive leads; and
    a processing unit configured to read impedances of the sensor pad, the processing unit comprising a controller and a communication interface, wherein the number of zones is equal to or greater than the number of conductive leads.

2. The moisture or fluid detection system of claim 1, further comprising a cable connecting a coupling unit and the processing unit.

3. The moisture or fluid detection system of claim 1, wherein the sensor pad contains two or more zones.

4. The moisture or fluid detection system of claim 3, wherein the number of zones is less than or equal to $n(n-1)/2$, where n is the number of conductive leads.

5. The moisture or fluid detection system of claim 4, wherein the area of each zone is within 10% of the mean area of all zones.

6. The moisture or fluid detection system of claim 4, wherein the interdigitated portion of each conductive lead is comprised of fingers, the size of each finger in a zone being within 10% of the mean size of all fingers in the zone.

7. The moisture or fluid detection system of claim 1, wherein the sensor pad is separated from the source of moisture by at least one additional substrate.

8. The moisture or fluid detection system of claim 7, wherein the at least one additional substrate is selected from the group comprising: a bed sheet, incontinence pad, diaper, or article of clothing.

9. The moisture or fluid detection system of claim 1, wherein the sensor pad is configured to maintain the spacing between each pair of conductive leads when the sensor pad is deformed.

10. The moisture or fluid detection system of claim 1, wherein the coupling unit is attachable to a patient support structure at or substantially at an edge of the patient support structure.

11. The moisture or fluid detection system of claim 1, wherein the plurality of conductive leads forms a single layer.

12. The moisture or fluid detection system of claim 1, wherein the coupling unit includes at least one sensor.

13. The moisture or fluid detection system of claim 1, wherein the processing unit is capable of communicating with at least one of a server, database, or device.

14. The moisture or fluid detection system of claim 1, wherein the processing unit comprises a signal analysis unit.

15. The moisture or fluid detection system of claim 1, wherein the system determines the presence or position of a patient as a function of at least one measured impedance.

16. The moisture or fluid detection system of claim 1, wherein the system determines a state of each zone based on the impedances, the states comprising: no person present-no moisture present, no person-moisture present, person present-no moisture present, and person-present-moisture present.

17. The moisture or fluid detection system of claim 1, wherein the coupling unit comprises an accelerometer, and wherein the system is configured to be in communication with a server or mobile device adapted for determining at least one of an individual's respiratory rate, body position or changes in body position, degree of movement, or sleeping pattern based on data from the accelerometer.

18. The moisture or fluid detection system of claim 1, wherein the first substrate consists of a mattress, cushion, or cover, and the conductive leads are disposed on the interior or exterior surface of the mattress, cushion, or cover.

19. A moisture or fluid detection system, comprising:
    a first substrate;
    a plurality of conductive leads disposed on the first substrate and defining at least one zone, each zone defined by an area in which one conductive lead is interdigitated with another conductive lead;
    a coupling unit coupled to at least two conductive leads; and
    a processing unit configured to read impedances of the sensor pad, the processing unit comprising a controller and a communication interface, wherein the number of zones is equal to or greater than the number of conductive leads.

* * * * *